United States Patent [19]

Sasa et al.

[11] Patent Number: 4,525,220
[45] Date of Patent: Jun. 25, 1985

[54] METHOD OF CLEANING ENDOSCOPE CHANNELS

[75] Inventors: Hiroyuki Sasa; Hisao Yabe; Yukio Nakajima; Fumiaki Ishii; Koji Takamura; Takeaki Nakamura, all of Tokyo, Japan

[73] Assignee: Olympus Optical Co., Ltd., Tokyo, Japan

[21] Appl. No.: 609,977

[22] Filed: May 14, 1984

[30] Foreign Application Priority Data

May 16, 1983 [JP] Japan ................................. 58-85552
May 16, 1983 [JP] Japan ................................. 58-85557

[51] Int. Cl.³ ............................ B08B 3/04; B08B 9/00
[52] U.S. Cl. .................................... 134/21; 134/22.12; 134/22.18; 134/24; 134/34; 422/33
[58] Field of Search .................... 134/21, 22.12, 22.18, 134/24, 166 C, 169 C, 171, 34; 128/6; 239/106, 112; 422/28, 33

[56] References Cited

U.S. PATENT DOCUMENTS 3,963,438  6/1976  Banez .

Primary Examiner—Marc L. Caroff

[57] ABSTRACT

In a method of cleaning an endoscope, the open end of a suction valve cylinder, arranged within a control section of the endoscope, is closed by a stop. A cap is mounted on the distal end of an insertion section so that liquid may flow between a nozzle and a suction opening which are arranged at the distal end of the insertion section. The nozzle communicates with an air supply channel and a liquid supply channel, and the suction opening communicates with a suction channel. A stop is mounted on the open end of an air/liquid supply valve cylinder arranged in the control section, and a syringe is connected to the stop. The piston of the syringe is pushed, thus supplying liquid in the cylinder of the syringe into the cylinder and discharging the liquid from the other ends of the three channels through the channels and the valve cylinders, thereby cleaning the interiors of these channels and valve cylinders with the liquid.

7 Claims, 3 Drawing Figures

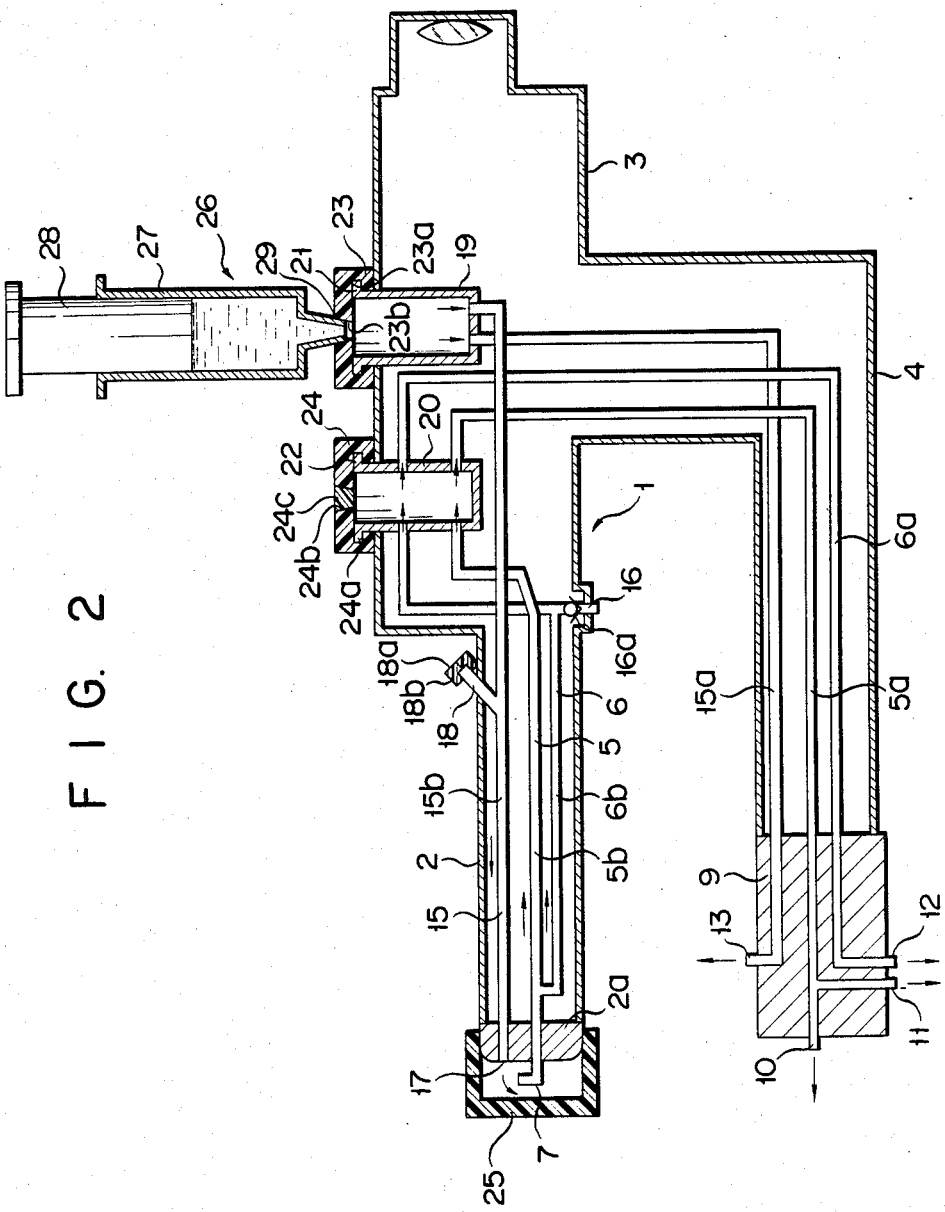
F I G. 2

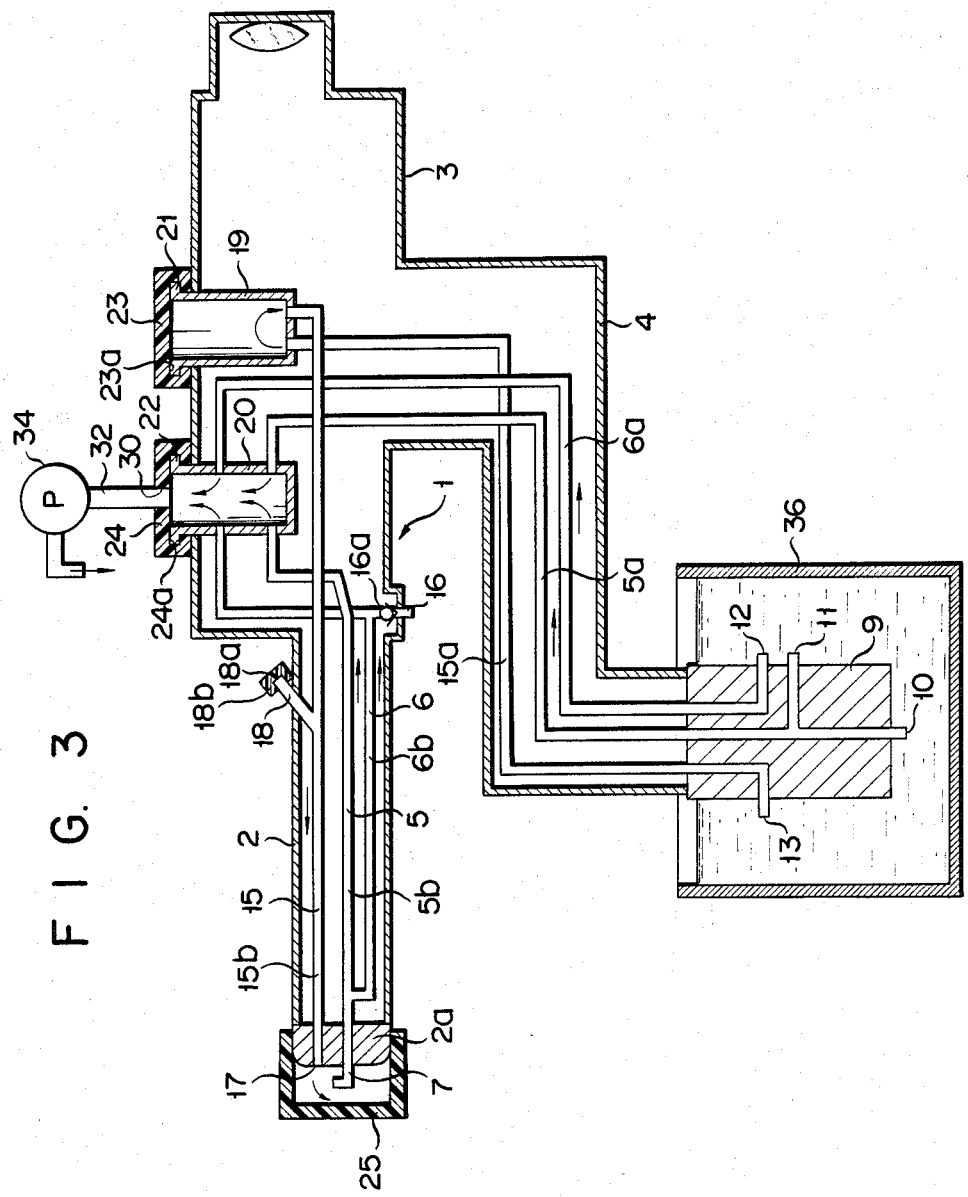

METHOD OF CLEANING ENDOSCOPE CHANNELS

BACKGROUND OF THE INVENTION

The present invention relates to a method of cleaning endoscopes.

An endoscope generally has various channels for supplying or sucking air or liquids. Therefore, when a used endoscope is to be cleaned, not only the outer surface thereof but also the channel interiors must be cleaned. The word "cleaning" used herein includes the steps of cleaning the channels with water to remove contaminants from the channels, then disinfecting the channels and again washing them with water. However, in the conventional method of cleaning channel interiors, a cleaning solution injection tube must be inserted into the port of each channel, and the valve of each channel must be opened. This requires connection of the cleaning solution injection tube into each channel and switching the valve of each channel. Procedures for cleaning the channels of an endoscope are, therefore, complex. With the conventional system as described above, there is an important problem in that incomplete cleaning frequently occurs, especially of the small portions of the valve body or the portion of the cylinder which is covered by the valve body.

In view of this problem, the present applicant has proposed, in Japanese Patent Disclosure No. 58-15836, a cleaning instrument for cleaning the channels of an endoscope, which is free from these problems. According to this invention, a cleaning solution is supplied through an air/liquid supply cylinder and a suction cylinder arranged in a control section of an endoscope so as to allow simultaneous cleaning of the interiors of the channels and the inner surfaces of the cylinders. More specifically, the valve bodies inserted into the air/liquid supply cylinder and suction cylinder are pulled out, and adaptors are inserted into the open cylinders. Liquid supply tubes connected to these adaptors are connected to a liquid supply pump. A liquid is supplied from the liquid supply pump to the respective cylinders. The liquid then flows from the cylinders to the suction opening and nozzle at the distal end of the endoscope and to the air supply port, liquid supply port and suction port of the connector through the liquid supply channel, the air supply channel and the suction channel, respectively, thereby cleaning these channels.

However, in this instrument, the adaptors must be inserted into both cylinders and liquid must be supplied to both cyliders. Therefore, operations for cleaning the channels of an endoscope are complex.

SUMMARY OF THE INVENTION

Accordingly, the object of the present invention is to provide a method of cleaning an endoscope, which makes it possible to easily and completely clean the channels and valve cylinders of an endoscope.

According to the invention there is provided a method of cleaning an endoscope which comprises a first step of closing one of the open ends of an air/liquid supply valve cylinder and a suction valve cylinder; a second step of mounting connecting means on the distal end of an insertion section so that liquid may flow between a nozzle and one end of a suction channel; and a third step of supplying or sucking liquid from the other of the open ends of the valve cylinders and sending the liquid through an air supply channel, a liquid supply channel, the suction channel and the valve cylinders, thereby cleaning the interiors of these channels and valve cylinders with the liquid.

BRIEF DESCRIPTION OF THE DRAWINGS

FIG. 2 is an sectional view of the endoscope showing how to clean it by a second method according to the invention; and FIG. 3 is a sectional view of the endoscope, showing how to clean the endoscope by a third method according to the invention.

DETAILED DESCRIPTION OF THE PREFERRED EMBODIMENTS

Figure 1:
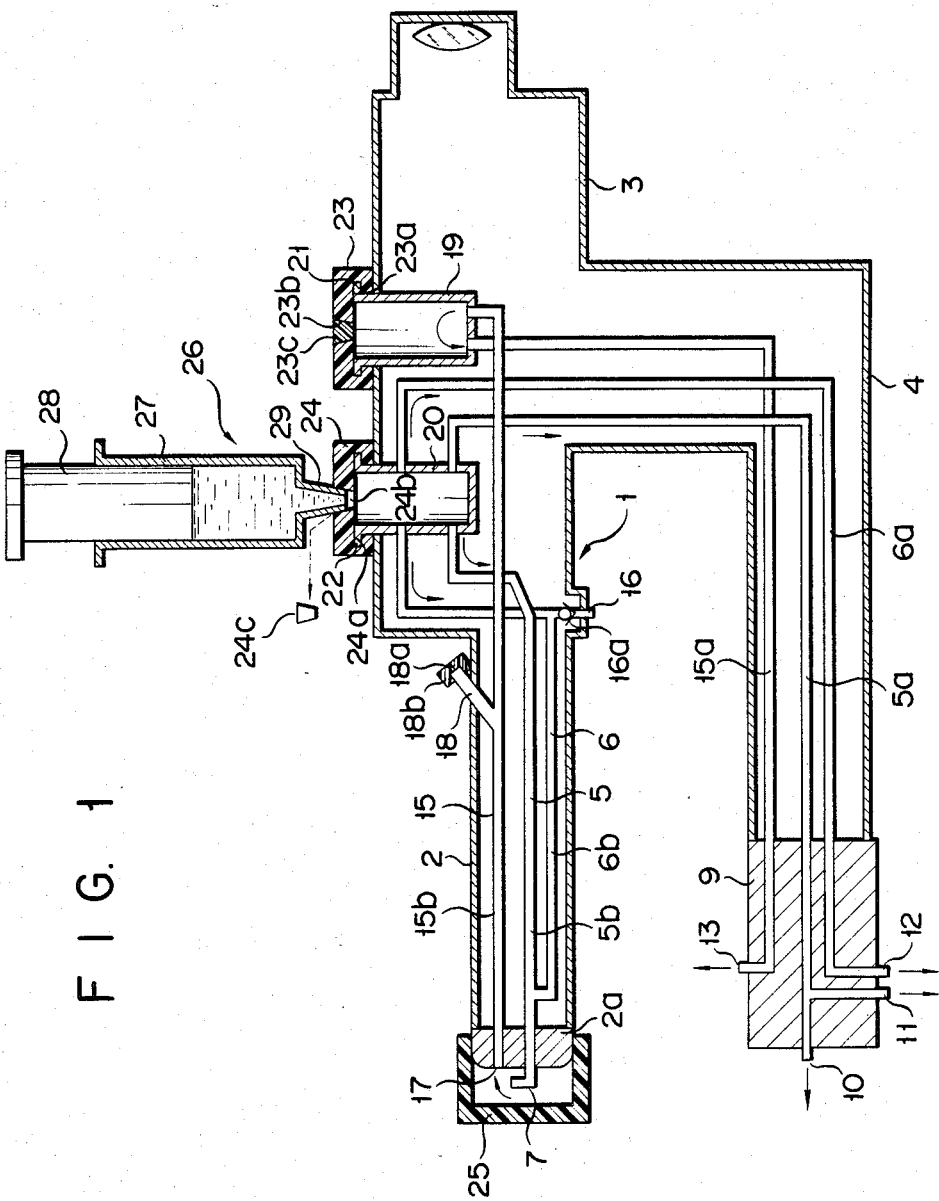
FIG. 1 is a sectional view of an endoscope, illustrating how to clean the endoscope by a first method according to the invention.

Some of the preferred embodiments of the present invention will now be described with reference to the accompanying drawings.

FIG. 1 shows an endoscope 1 comprising a control section 3, an insertion section 2 extending from the control section 3 and a light guide cable 4 extending from the control section 3. Various channels are formed inside the endoscope 1. First, an air supply channel 5 and a liquid supply channel 6 are formed extending through the insertion section 2, the control section 3 and the light guide cable 4. The distal ends of these channels 5 and 6 are connected to an air/liquid supply nozzle provided at the distal end 2a of the insertion section 2. The nozzle 7 is arranged to face the outer surface of an observation window (not shown) for spraying air or a liquid against it. The light guide cable 4 has a connector 9 at the free end. The connector 9 has first and second air supply ports 10 and 11 both communicating with the air supply channel 5, a liquid supply port 12 communicating with the liquid supply channel 6, and a suction port 13 communicating with a suction channel. When the connector 9 is connected to a light source device (not shown), the first air supply port is connected to an air supply pump in the light source device. The second air supply port 11 and the liquid supply port 12 are connected to a liquid supply tank (not shown).

A suction channel 15 extends along the entire length of the insertion section 2, the control section 3 and the light guide cable 4. That end portion of the suction channel 15 which is at the side of the insertion section 2 serves as an instrument insertion channel 15b. The distal end of the instrument insertion channel 15b communicates with a suction opening 17, which opens to the distal end face of the insertion section 2. The proximal end of the instrument insertion channel 15b opens externally at the control section 3 to form a forceps port 18. The forceps port 18 is closed with a detachable stop 18b having a small hole 18a. A sub liquid port 16 having a check valve 16a communicates with the liquid supply channel 6.

The instrument insertion channel 15b is connected to the proximal end of the remaining portion of the suction channel 15 through a suction cylinder, that is, a suction valve cylinder 19. An air/liquid supply cylinder or air/liquid supply valve cylinder 20 is inserted midway along both the air supply channel 5 and the liquid supply channel 6. The valve cylinders 19 and 20 are arranged next to each other at a side surface of the control section 3. The upper ends of the valve cylinders 19 and 20 open to the outside of the control section 3. The suction valve cylinder 19 has a bottom and a flange 21 formed integrally therewith at its open edge or upper edge. The air/liquid supply valve cylinder 20 similarly has a bottom and a flange 22 formed integrally therewith at its open edge. Stops 23 and 24 are attached to the valve cylinders 19 and 20, respectively, to close their open ends. Engagement grooves 23a and 24a, engaging with the flanges 21 and 22, are formed in the inner surfaces of the stops 23 and 24, so as to prevent the stops from being inadvertently removed even if the pressure rises in the cylinders 19 and 20. The stops 23 and 24 have connecting ports 23b and 24b. Detachable closing members 23c and 24c are fitted to the connecting ports 23b and 24b, respectively.

Pistons (not shown) are generally inserted in the suction valve cylinder 19 and the air/liquid supply valve cylinder 20. These pistons serve to allow or block communication between upstream portions and downstream portions of the air supply channel 5, the liquid supply channel 6 and the suction channel 15, respectively. However, when the stops 23 and 24 are to be mounted on the cylinders 19 and 20, respectively, the pistons are removed first.

The method of cleaning the endoscope 1 will now be described.

First, as shown in FIG. 1, the stops 23 and 24 are attached to the cylinders 19 and 20, respectively. Then, a detachable cap 25 made of resilient material such as rubber is mounted on the distal end of the insertion section 2 so that liquid may flow between the nozzle 7 and suction opening 17. The closing member 24c is removed from the stop 24 to open the connecting port 24b. The connecting port 23b is closed by the member 23c. A syringe 26 as liquid supplying means is then connected to the connecting port 24c. The syringe has a cylinder 27 with a liquid injection port 29 at its one end and a piston 28 inserted into the cylinder 27. The injection port 29 is connected to the connecting port 24c.

When the piston 28 is pushed in this condition, liquid in the cylinder 27 is compressed by the piston and flows into the valve cylinder 20 through the connecting port 24c. The liquid then flows into the downstream portions 5b and 6b of the channels 5 and 6 and into the upstream portions 5a and 6a. The liquid which has flowed into the downstream portions 5b and 6b enters into the cap 25 through the nozzle 7 and then flows into valve cylinder 19 through the suction opening 17 and the downstream portion 15b of the suction channel 15. It flows from the cylinder 19 into the upstream portion 15a and finally flows out from the suction port 13. At the same time, the liquid which has flowed into the upstream portions 5a and 6a is discharged from the first and second air supply ports 10, 11 and the liquid supply port 12. Due to this flow, the channels 5, 6 and 15 can be cleaned along their entire length, and the cylinders 19 and 20 can be simultaneously cleaned. When the liquid enters into the downstream portion 15b of the suction channel 15, some of this liquid flows out through the small hole 18a in the stop 18b, and the interior of the forceps port 18 can thus be cleaned.

In the above description, the liquid is water or a disinfectant. In general, disinfection is performed with disinfectant. However, the term "cleaning" used herein includes both washing and disinfection or sterilization.

In the first embodiment of this invention described above, all the channels and cylinders of an endoscope can be easily and completely cleaned, by supplying liquid from only one place. Thus excellent operability can be obtained.

In the first embodiment, liquid is supplied from the air/liquid supply valve cylinder 20. However, as shown in FIG. 2, liquid can be supplied from the suction valve cylinder 19. In this embodiment, the connecting port 24b of the stop 24 is closed by the closing member 24c, and the syringe 26 is connected to the connecting port 23b of the stop 23. When the piston 28 is pushed, the liquid in the cylinder 26 flows into the suction valve cylinder 19. Part of the liquid is discharged from the suction port 13 through the upstream portion 15a of the suction channel 15. The remainder of the liquid which has flowed into the cylinder 19 is discharged from the first and second supply ports 10, 11 and liquid supply port 12 through the downstream portion 15b, the interior of the cap 25, the downstream portions 5b and 6b, the air/liquid supply valve cylinder 20, and the upstream portions 5a and 6a. As a result, all the channels and cylinders of the endoscope 1 can be simultaneously cleaned, as in the first embodiment.

In the first and second embodiment, the liquid supplying means is not limited to a syringe, it may be a combination of an air pump and a liquid tank.

FIG. 3 shows how to clean the endoscope 1 by another method according to the invention. In this embodiment, first, stops 23 and 24 are attached to the valve cylinders 19 and 20 to close the open ends thereof. The stops 23 and 24 have engagement grooves 23a and 24a which engage with the flanges 21 and 22 of the cylinders 19 and 20. The stop 24 has a connecting port 30 to which one end of a suction tube 32 is connected. The other end of the tube 32 is connected to a suction pump. A detachable cap 25 is mounted on the distal end of the insertion section 2 so that liquid may flow between the nozzle 7 and suction opening 17. The connector 9 is submerged in liquid held in a liquid tank 36.

When the pump 34 is operated under this condition, the interior of the air/liquid supply valve cylinder 20 is kept at a negative pressure. Then, the interiors of the upstream portions 5a and 6a and the downsteam portions 5b and 6b of the channels 5 and 6 are kept at a negative pressure. Since the suction opening 17 communicates with the nozzle 7 through the interior of the cap 25, the interiors of the suction channel 15 and suction valve cylinder 19 are also kept at a negative pressure. When the channels 5, 6 and 15 and the valve cylinders 19 and 20 are kept at a negative pressure, the liquid in the tank 36 is sucked from the ports 10, 11, 12 and 13 into the upstream portions 5a, 6a and 15a. The liquid flows from the upstream portions 5a and 6a into the valve cylinder 20 and is sucked into the pump 34. The liquid also from the upstream portion 15a into the interior of the cap 25 through the valve cylinder 19 and downstream portion 15b. Then it is sucked into the pump 34 through the downsteam portions 5b and 6b and valve cylinder 20. Due to this flow, all the channels and valve cylinders of the endoscope 1 can be cleaned simultaneously.

In the third embodiment, the liquid is sucked from the air/liquid supply valve cylinder 20. However, liquid can be sucked from the suction valve cylinder 19. In this case, all the channels and valve cylinders of the endoscope can be cleaned, as in the third embodiment. Moreover, the means for sucking liquid is not limited to a suction pump, it may be a piston-type syringe, for example. Although the first and second embodimehts are used to clean an endoscope which does not have a gas supply valve or a gas supply channel, the present invention can be similarly applied to an endoscope which has a gas supply valve and a gas supply channel. Further, the present invention can be applied to an endoscope in which an air supply channel and a liquid supply channel communicate with two nozzles provided at a distal end of the insertion section of the endoscope.

What is claimed is:

1. A method of cleaning channels of an endoscope which includes a control section, an insertion section extending from the control section and having a nozzle at its distal end, a light guide cable extending from the control section and having a connector at its distal end, an air supply channel extending in the endoscope and having one end communicating with the nozzle and the other end opening to the connector, a liquid supply channel extending in the endoscope and having one end communicating with the nozzle and the other end opening to the connector, a suction channel extending in the endoscope and having one end opening to the distal end of the insertion section and the other end opening to the connector, an air/liquid supply valve cylinder arranged in the control section to communicate with the air supply channel and liquid supply channel and having one end opening to the outside of the control section, and a suction valve cylinder arranged in the control section to communicate with the suction channel and having one end opening to the outside of the control section; said method comprising:

a first step of closing one of the open ends of the air/liquid supply valve cylinder and suction valve cylinder;

a second step of mounting connecting means on the distal end of the insertion section so that liquid is confined to flow between the nozzle and said one end of the suction channel; and a third step of supplying or sucking liquid from the other of the open ends of the valve cylinders and sending the liquid through the three channels, the air/liquid supply valve cylinder and the suction valve cylinder, thereby cleaning the interiors of the channels and valve cylinders with the liquid.

2. A method according to claim 1, wherein said first step includes closing the open end of the suction valve cylinder; and said third step includes supplying liquid from the open end of the air/liquid supply valve cylinder into the air/liquid supply valve cylinder and discharging the liquid from the other ends of the air supply channel, liquid supply channel and suction channel through the three channels and the suction valve cylinder.

3. A method according to claim 1, wherein said first step includes closing the open end of the air/liquid supply valve cylinder; and said third step includes supplying liquid from the open end of the suction valve cylinder into the suction valve cylinder and discharging the liquid from the other ends of the air supply channel, liquid supply channel and suction channel through the three channels and the air/liquid supply valve cylinder.

4. A method according to claim 1, wherein said first step includes closing the open end of the suction valve cylinder; and said third step includes bringing the other ends of the air supply channel, liquid supply channel and suction channel into contact with liquid, and sucking the liquid from the open end of the air/liquid supply valve cylinder through the three channels and the valve cylinders.

5. A method according to claim 4, wherein said third step includes submerging the connector in liquid.

6. A method according to claim 1, wherein said first step includes closing the open end of the air/liquid supply valve cylinder; and said third step includes bringing the other ends of the air supply channel, liquid supply channel and suction channel into contact with liquid, and sucking the liquid from the open end of the suction valve cylinder through the three channels and the valve cylinders.

7. A method according to claim 6, wherein said third step includes submerging the connector in liquid.

* * * * *